(12) United States Patent
Ichiro et al.

(10) Patent No.: US 7,589,189 B2
(45) Date of Patent: Sep. 15, 2009

(54) INHIBITION OF THE EXPRESSION OF HUNTINGTIN GENE

(75) Inventors: Kanazawa Ichiro, Tokyo (JP); Liu Wanzhao, Tokyo (JP); Yu-Lai Wang, Tokyo (JP); Keiji Wada, Tokyo (JP); Jun Goto, Tokyo (JP); Miho Murata, Tokyo (JP)

(73) Assignee: Japan Science and Technology Agency, Saitama (JP)

(*) Notice: Subject to any disclaimer, the term of this patent is extended or adjusted under 35 U.S.C. 154(b) by 223 days.

(21) Appl. No.: 10/556,711

(22) PCT Filed: Apr. 30, 2004

(86) PCT No.: PCT/JP2004/006360

§ 371 (c)(1),
(2), (4) Date: Nov. 13, 2006

(87) PCT Pub. No.: WO2004/101787

PCT Pub. Date: Nov. 25, 2004

(65) Prior Publication Data

US 2008/0015158 A1  Jan. 17, 2008

(30) Foreign Application Priority Data

May 14, 2003 (JP) ............................ 2003-136477

(51) Int. Cl.
- A01N 43/04 (2006.01)
- A61K 31/70 (2006.01)
- C07H 21/02 (2006.01)
- C07H 21/04 (2006.01)

(52) U.S. Cl. .................. 536/24.5; 536/23.1; 536/24.3; 536/24.33; 514/44

(58) Field of Classification Search ............... 536/23.1, 536/24.3, 24.33, 24.5; 514/44
See application file for complete search history.

(56) References Cited

U.S. PATENT DOCUMENTS 5,693,757 A  12/1997  MacDonald et al.

(Continued)

FOREIGN PATENT DOCUMENTS

CA  2507606 A1  6/2004

(Continued)

OTHER PUBLICATIONS

Yen et al. (Annuals of Neurology, 1999 vol. 46:366-373).*

(Continued)

*Primary Examiner*—Sean McGarry
*Assistant Examiner*—Terra Cotta Gibbs
(74) *Attorney, Agent, or Firm*—Alston & Bird LLP

(57) ABSTRACT

It is intended to provide methods for suppressing the huntington gene expression by using a double-stranded RNA (dsRNA), huntington gene expression inhibitors to suppress the huntington gene expression, and preventives and/or remedies of Huntington's disease. Targeting against a specific sequence of mRNA at immediately upstream of CAG repeats in HD genes of Huntington's disease, the huntington gene expression is suppressed by using a dsRNA homologous to the sequence. In this invention, a short siRNA (short double-stranded RNA) having bp as short as around 21-23 bp can be effectively used as the dsRNA homologous to a specific RNA sequence in a region at immediately upstream of CAG repeats. The dsRNA of this present invention can be used as a huntington gene expression inhibitor, or a preventive and/or a remedy of Huntington's disease by administering or introducing into a living body or a living cell in mammals for the prevention and/or treatment of Huntington's disease.

10 Claims, 10 Drawing Sheets

U.S. PATENT DOCUMENTS 7,320,965 B2 * 1/2008 Sah et al. .................. 514/44

FOREIGN PATENT DOCUMENTS

| EP | 0 614 977 B1 | 9/1994 |
|---|---|---|
| WO | WO 00/52210 | 9/2000 |
| WO | WO 2004/047872 A2 | 6/2004 |

OTHER PUBLICATIONS

Haque et al. (Experimental Neurology, 1997 vol. 144:139-146).*
GenBank Accession No. L12392, *Homo sapiens* Huntington's Disease (HD) mRNA, May 13, 2002.*
Hammond et al. (Nature Reviews, 2001 vol. 2:110-119).*
Schwartz et al. (Current Opinion in Molecular Therapeutics, 2000 vol. 2:162-167).*
Goto, J., et al., "Suppression of Huntingtin Gene Expression by siRNA: A Possible Therapeutic Tool for Huntington's Disease," *Neurology*, 2003, p. A286, vol. 60, No. 5, Suppl. 1.
Liu, W., et al., "Specific Inhibition of Huntington's Disease Gene Expression by siRNAs in Cultured Cells," *Proc. Jpn. Acad. Ser. B.*, Dec. 2003, pp. 293-298, vol. 79B(10).
Caplen et al., "Rescue of polyglutamine-mediated cytotoxicity by double-stranded RNA-mediated RNA interference," *Human Molecular Genetics*, 2002, vol. 11(2), pp. 175-184.
Persichetti et al., "Normal and Expanded Huntington's Disease Gene Alleles Produce Distinguishable Proteins Due to Translation Across the CAG Repeat," *Molecular Medicine*, (1995), vol. 1(4), pp. 374-383.
Goto, J. et al., "Suppression of Huntingtin Gene Expression by SiRNA: A Possible Therapeutic Tool for Huntington's Disease," *Neurology*, 2003, p. A286, vol. 60, No. 5, Suppl. 1.

* cited by examiner

Fig. 1

INHIBITION OF THE EXPRESSION OF HUNTINGTIN GENE

TECHNICAL FIELD

The present invention relates to the use of RNAi (RNA interference) method, to double-stranded RNAs (siRNA: small interfering RNA) composed of sense- and antisense-strand RNAs which are homologous to the specific sequences targeted by huntingtin mRNAs capable of suppressing the huntingtin gene expression, to huntingtin gene expression inhibitors composed of the double-stranded RNAs, to preventives and/or remedies of Huntington's disease containing the expression inhibitors as an active ingredient, and the like.

BACKGROUND ART

Huntington's disease (HD) is a progressive neurodegenerative disorder characterized by the expressions of involuntary movements (chorea), dementia, and psychiatric disorders (J. Med. 315, 1267-1276, 1986). The disease generally develops during the middle ages of 30-50 years old, however some of the cases may develop very earlier or later in life than the ages. The symptom is progressive, and most of the cases result in death in 10-20 years after the development of the secondary complication of the involuntary movements. By the examination of individual brains after the death resulting from Huntington's disease, a selective loss of neuronal cells was proved to affect to the striatum. A huntingtin gene, which is the causative gene for Huntington's disease, is mapped in a region of 2.2 Mb located between loci D4S126 and D4S98 in cellular genetic sub-band at the end of the short arm of chromosome 4 in human (Neuron 3, 183-190, 1989, J. Hum. Genet. 49, 7-16, 1991, Am. J. Hum. Genet. 51, 357-362, 1992).

Huntington's disease is a genetic neurodegenerative disorder resulted from progressively losing brain striatum neuronal cells after CAG repeats expanded in exon 1 of huntingtin gene transcription and translated into polyglutamine (poly Q) tract (Annu. Rev. Med. 47, 201-209, 1996) In other words, Huntington's disease is caused by abnormally expanded CAG repeats on the exon 1 portion of huntingtin gene and results in the selective loss of brain striatal nerves. The huntingtin gene codes for cytoplasmic protein of molecular weight 348 kDa called huntingtin, widely expresses in both central nervous system (CNS) and non-central nervous system (non-CNS) tissues. The CGA triplet sequence (CAG triplets) of HD gene is translated into polyglutamine (poly Q) in huntingtin protein. Typically, normal and mutant huntingtin alleles carry 6 to 37 and 35 to 180 CAG repeats, respectively.

In recent years, as a method for the treatment of Huntington's disease, methods of treating huntingtin genes, targeting huntingtin genes, using antagonistic substances against huntingtin protein expressing huntingtin genes, and the like, have been disclosed. For example, Publication of Japanese Laid-Open Patent Application No. 1995-67661 discloses the treatment methods of: substituting mutant huntingtin genes for normal genes after inserting DNAs expressing normal huntingtin proteins into cells of patients; introducing genes that encode sequences capable of transcribing and expressing antisense RNAs of huntingtin genes of Huntington's disease, into cells of patients; administering antagonists to huntingtin proteins of Huntington's disease; or the like. As a treatment method of autosomal dominant disorders such as Hunton's disease, the treatment method by the allele-specific targeting that targets against RNAs of Huntington's disease, has been also disclosed in Published Japanese translation of PCT international publication No. 2003-503008. However, when considered from the viewpoints of the complication and stability of introducing genes, or the treatment effect obtained, these treatment methods have not always worked out as expected.

On the other hand, in some kind of creature (Caenorhabditis elegans), it has been recently found that the gene expression can be specifically inhibited by double-stranded RNAs (Nature 391, 806-811, 1998, WO99/32619). This phenomenon is that double-stranded RNAs (dsRNAs) composed of sense- and antisense-strand RNAs, which are homologous to certain genes, destroy the homologous part in the transcription products (mRNAs) of the genes, and called RNAi (RNA interference). Later the phenomenon was found in lower eukaryotic cells including various kinds of animals (Cell 95, 1017-1026, 1998, Proc. Natl. Acad. Sci. USA 95, 14687-14692, 1998, Proc. Natl. Acad. Sci. USA 96, 5049-5054, 1999) and plants (Proc. Natl. Acad. Sci. USA 95, 13959-13964, 1998).

In the early days of the discovery, RNAi was believed to be difficult to use in mammalian cells, since apoptosis was induced by underlying immune function in cells and the cells died, when around 30 or more bp of dsRNAs were introduced into the cells. However, RNAi was also identified to occur in mouse early embryos and in mammalian cultured cells in 2000, and it has become apparent that the RNAi induction mechanism itself also exists in mammalian cells (FEBS Lett 479, 79-82, 2000, WO01/36646).

If the expression of certain genes or gene clusters is inhibited in mammals by using such an RNAi function, it would be apparently useful. Since many of the diseases (such as cancer, endocrine disease, and immunological disease) are developed by abnormal expression of certain genes or gene clusters in mammals, the inhibition of the genes or gene clusters may be used to treat these symptoms. In addition, diseases may be developed due to the expression of mutant protein, in these cases, the diseases can be treated by suppressing the mutant allele expression. Furthermore, such gene-specific inhibition can be used for the treatment of viral disease that was caused by, for example, retrovirus (viral genes in retrovirus are incorporated into their host genome and expressed) such as HIV.

The dsRNAs inducing the function of RNAi were initially considered to require the introduction of around 30 or more bp of dsRNAs into the cells, however, it has recently become apparent that the shorter (21-23 bp) dsRNAs (short double-stranded RNAs: siRNA; small interfering RNA) can induce RNAi without exhibiting cytotoxicity even in mammalian cell system (Nature 411, 494-498, 2001). The siRNA is recognized as a powerful tool to suppress gene expression at all the developmental stages of somatic cells, and can be expected as a method to suppress disease-causing gene expression before the development of the disease in progressive genetic diseases and the like. But it has not been reported yet that a method to suppress gene-specific expression by using such dsRNAs, effectively applied for the genetic disease of Huntington's disease (HD).

The subject of the present invention is to provide the double-stranded RNAs (siRNAs) composed of sense- and antisense-strand RNAs homologous to the certain sequences targeted by huntingtin mRNAs which can suppress the expression of huntingtin gene, the huntingtin gene expression inhibitors composed of the double-stranded RNAs, the preventives and/or the remedies for Huntington's disease containing the expression inhibitor as an active ingredient, and the like.

Huntington's disease is a genetic neurodegenerative disorder resulted from progressively losing brain striatal neuronal cells after CAG repeats expanded in exon 1 of huntingtin gene transcription and translated into polyglutamine (poly Q) tract. When the huntingtin mRNAs at upstream of CAG repeats were examined, the present inventors found two sites containing the specific sequences which are effective targets of siRNAs. Consequently, as the dsRNA sequences homologous to these sequences; a) siRNA-5'UTR targeting 5'-untransrated region, and; b) siRNA-HDexon 1 targeting a region at immediately upstream of CAG repeats, furthermore; c) as currently known, for the only difference between normal and mutant huntingtin genes is the lengths of the CAG repeats, three siRNAs of siRNA-CAG were made directly targeting the CAG repeats, after analyzing the effect of the siRNAs by using tissue culture models or Huntington's disease mouse models, it was found that the siRNA-HDexon 1 quite efficiently suppressed the huntingtin gene expression and the development of Huntington's disease, then the present invention was completed.

DISCLOSURE OF THE INVENTION

The present invention relates to: (1) a double-stranded RNA composed of sense- and antisense-strand RNAs, homologous to a certain sequence targeted against a huntingtin mRNA, which can inhibit huntingtin gene expression; (2) the double-stranded RNA according to ("1"), wherein the certain sequence targeted against a huntingtin mRNA comprises an RNA derived from a base sequence shown in SEQ ID NO: 1 in the sequence listing; (3) the double-stranded RNA according to ("1") or ("2"), wherein the certain sequence targeted against a huntingtin mRNA is a base sequence composed of 19 to 24 base pairs; (4) the double-stranded RNA according to any one of ("1") to ("3"), wherein the RNA derived from the base sequence shown in SEQ ID NO: 1 is an RNA derived from a region at immediately upstream of CAG repeats of exon 1 of a huntingtin gene; (5) the double-stranded RNA according to any one of ("1") to ("4"), wherein the RNA derived from a region at immediately upstream of CAG repeats of exon 1 of a huntingtin gene is composed of base sequences shown in SEQ ID NOs: 3 and 41 in the sequence listing; (6) the double-stranded RNA according to ("1"), composed of a base sequence wherein one or few bases are deleted, substituted, or added in a base sequence shown in SEQ ID NO: 3 in the sequence listing, and the complementary base sequence thereof; (7) the double-stranded RNA according to any one of ("1") to ("6") prepared from synthesized sense- and antisense-strand RNAs; (8) the double-stranded RNA according to any one of ("1") to ("6"), which is prepared from sense- and antisense-strand RNAs generated by using gene recombination; (9) the double-stranded RNA according to ("8"), wherein the sense- and antisense-strand RNAs generated by using gene recombination are prepared by obtaining RNAs which are generated by introducing a expression vector incorporated DNA capable of transcribing respectively the RNAs, into a host cell.

The present invention further relates to: (10) a huntingtin gene expression inhibitor composed of the double-stranded RNA according to anyone of ("1") to ("9"); (11) a huntingtin gene expression inhibitor composed of a fusion product, wherein the double-stranded RNA according to any one of ("1") to ("9") is added to a TAT sequence, a protein transduction domain derived from HIV-1; (12) a huntingtin gene expression inhibitor composed of a complex formed from the double-stranded RNA according to any one of ("1") to ("9") and a positively-charged ribosome/lipid; (13) a huntingtin gene expression inhibitor composed of an expression vector incorporating a DNA capable of transcribing the double-stranded RNA according to any one of ("1") to ("6").

The present invention still further relates to: (14) a method for suppressing the expression of a huntingtin gene in a living body or living cell of a mammal, wherein the huntingtin gene expression inhibitor according to any one of ("10") to ("13") is introduced into a living body or living cell of a mammal; (15) a preventive and/or a remedy of Huntington's disease containing the huntingtin gene expression inhibitor according to any one of ("10") to ("13") as an effective ingredient; (16) the preventive and/or the remedy of Huntington's disease according to ("15") further containing a pharmaceutically acceptable carrier; (17) a method for preventing the development and/or treatment for Huntington's disease, wherein the preventive and/or the remedy of Huntington's disease according to ("15") or ("16") is introduced into a living body or living cell of a mammal.

BRIEF DESCRIPTION OF DRAWINGS

FIG. 1 shows the sequences of siRNAs and the target positions in the Example of the present invention, Top: nucleotide sequence corresponds to SEQ ID NO:1, amino acid sequence corresponds to SEQ ID NO:2. Bottom: siRNA-5' UTR,5' to 3' corresponds to SEQ ID NO:5, 3' to 5' corresponds to SEQ ID NO:6; siRNA-HDExon 1, 5' to 3' corresponds to SEQ ID NO:3, 3' to 5' corresponds to SEQ ID NO:4; siRNA-CAG, 5' to 3' corresponds to SEQ ID NO:7, 3' to 5' corresponds to SEQ ID NO:8.

BEST MODE OF CARRYING OUT THE INVENTION

Figure 2:
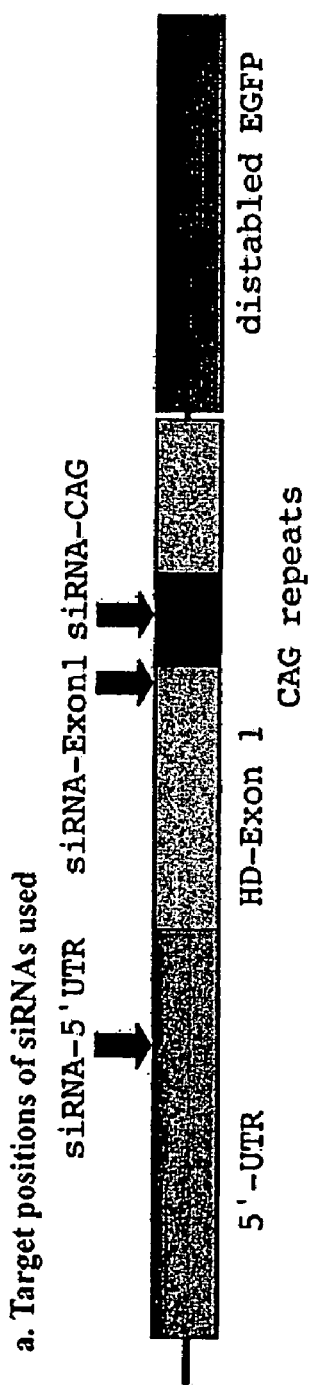
FIG. 2 shows the target positions of siRNAs and the expression constructs of pd1EGFP N1 in the Example of the present invention. Specifically, a. shows the target positions of siRNAs (black arrows), b. shows pd1EGFP N1 plasmid, and c. shows the expression constructs of pd1EGFP N1 to which HD exon 1 containing various numbers of CAG repeats (poly Q) is inserted.
Figure 2:
Figure 2:
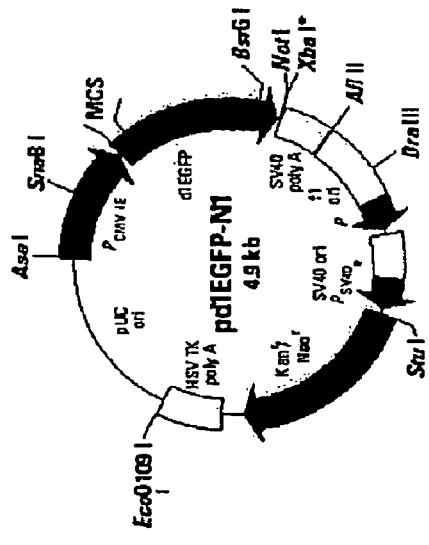

The double-stranded RNAs of the present invention are not particularly limited as long as they are comprised of sense- and antisense-strand RNAs homologous to the certain sequence targeted against huntingtin mRNA, which is capable of suppressing the huntingtin gene expression. The huntingtin gene is preferably derived from human, but not limited thereto. As the above-mentioned huntingtin gene, the exon 1 of huntingtin gene composed of the base sequence shown in SEQ ID NO: 1 in the sequence listing (NCBI accession NO: L12392 and the $1^{st}$ to $584^{th}$ of NM_002111; SEQ ID NO: 1, the corresponding amino acid sequence of the gene is shown in SEQ ID NO: 2) (Cell 72, 6, 971-983, 1993) can be exemplified.

The certain sequence to be targeted by the above-mentioned huntingtin mRNA is partial sequence of a certain region of huntingtin mRNA; preferably partial sequence with the lengths of 19 to 24 bp, more preferably 21 to 23 bp, more preferably still 21 bp. As the target sequence of the huntingtin mRNA, the RNA derived from a region at immediately upstream of CAG repeats of the exon 1 of huntingtin gene, particularly the RNA derived from the base sequence of the $343^{rd}$ to $363^{rd}$ of base sequence shown in SEQ ID NO: 1 in the sequence listing can be preferably exemplified.

Futher, the sense-strand RNA homologous to the certain sequence to be targeted by huntingtin mRNA is the RNA derived from such as the base sequence of the $343^{rd}$ to $363^{rd}$ of base sequence shown in the above-mentioned SEQ ID NO: 1, and the antisense-strand RNA homologous to the certain sequence to be targeted by huntingtin mRNA is the complementary RNA to the above sense-strand RNA, specifically, GCCUUCGAGUCCCUCAAGUCC (SEQ ID NO: 3) for sense-strand RNA, and UCCGGAAGCUCAGGGAGUUCA (SEQ ID NO: 4) for antisense-strand RNA can be preferably exemplified. Also GAUGGACGGCCGCUCAGGUUU (SEQ ID NO: 5) for sense-strand RNA, and UUCUAC-CUGCCGGCGAGUCCA (SEQ ID NO: 6) for antisense-strand RNA can be exemplified.

The double-stranded RNA of the invention is usually constructed as siRNA in which a sense-strand RNA and an antisense-strand RNA are bound to each other, but as a matter of practical convenience, the double-stranded RNA constructed as siRNA which is comprised of the mutant sense-strand RNA sequence wherein one or few bases are deleted, substituted, and added in the sense-strand RNA sequence; and the mutant antisense-strand RNA sequence complementary to the mutant sense-strand RNA sequence; is also contained in the scope of the present invention. The above-mentioned "sequence wherein one or few bases are deleted, substituted, and added" is, for example, intended the base sequence deleted, substituted, and added by any number of bases from 1 to 5 bases, preferably 1 to 3 bases, more preferably 1 to 2 bases, more preferably still one base.

In order to generate the double-stranded RNA (dsRNA) of the present invention, well-known methods such as methods by synthesis and by using gene-recombination technology can be conveniently used. In the method by synthesis, the double-stranded RNA can be synthesized based on the sequence information in the usual manner. In the method by using gene-recombination technology, the double -stranded RNA can be generated by the follwing steps: constructing expression vectors to which sense- and antisense-strand DNAs are incorporated; introducing the vectors into host cells; then, obtaining sense- and antisense-strand RNAs generated by transcription, respectively. Furthermore, by expressing the RNA forming hairpin structure with a sense-strand DNA-linker-antisense-strand DNA of the certain sequence of huntingtin gene, the desired double-stranded RNA may be generated.

As for the huntingtin gene expression inhibitor of the present invention; the double-stranded RNA (dsRNA) of the invention mentioned above; the fusion product wherein the double-stranded RNA is added to a TAT sequence, protein transduction domain derived from HIV-1; the complex formed from the double-stranded RNA and a positively-charged ribosome/lipid; or the expression vector to which the DNA capable of transcribing the double-stranded RNA is incorporated, can be exemplified. As for the above-mentioned expression vector, viral vectors such as lentiviral vectors, herpesvirus (HSV) vectors, adenoviral vectors, and human immunodeficiency virus (HIV) vectors; and plasmids for the expression of animal cells, can be exemplified.

The preventive and/or remedy of Huntington' s disease of the present invention is not especially limited, except that it should contain the huntingtin gene expression inhibitors of the invention mentioned above as an effective ingredient, and pharmaceutically acceptable carriers used ordinary within the pharmaceutical field, for example, various compounding ingredients for preparation such as binders, stabilizers, excipients, diluents, pH buffers, disintegrating agents, solubilizers, solubilizing agents, isotonic agents can be used together. Pharmaceutical compositions used with the pharmaceutically acceptable carrier, can be prepared with the formulation well-known in themselves within the pharmaceutical field depending on the forms of administrations, such as oral (including buccal or sublingual) or parenteral administration (for example, injectable solution).

In addition, the method for suppression of huntingtin gene expression, or for prevention and/or treatment of Huntington's disease of the present invention, is not especially limited, except for the methods for introducing the expression inhibitors or preventives and/or remedies of Huntington's disease of the present invention into living bodies, tissues, or cells in mammals, for example, the gene which transcribes each RNA of double-stranded RNAs or the double-stranded RNAs with hairpin structure, can be introduced into the living bodies or living cells in mammals by gene transfer methods well-known in themselves. The examples of the gene transfer methods are as follows. (1) Intracranial injection method: in fetal or neonatal periods; well-known viral vectors or plasmids which can be synthesized in living bodies, and into which double-stranded RNAs, siRNAs are incorporated; TAT-siRNAs; or positively-charged ribosomes/lipids-siRNA complexes; are directly injected into a brain. In maturation period, they are administrated into a brain ventricle. (2) Pulse injection method by veins of limbs or tails: in a short period of time, with a good amount of well-known viral vectors or plasmids which can be synthesized in living bodies, and into which double-stranded RNAs, siRNAs are incorporated; or positively-charged ribosomes/lipids-siRNA complexes; are injected. (3) Intraperitoneal administration: well-known viral vectors, which can be synthesized in living bodies, and into which siRNAs are incorporated; or TAT-siRNAs; are injected. (4) Nasal instillation: well-known viral vectors which can be synthesized in living bodies, and into which double-stranded RNAs, siRNAs are incorporated; or TAT-siRNAs; are absorbed from nasal mucosa.

The present invention will be described more specifically with example, but the technical scope of the present invention is not limited to the following example.

EXAMPLE 1

[Materials and methods]

(Preparation of siRNAs) As an antisense-strand RNA, there is a sequence of UCCGGAAGCUCAGGGAGUUCA (SEQ ID NO: 4).

Figure 1:
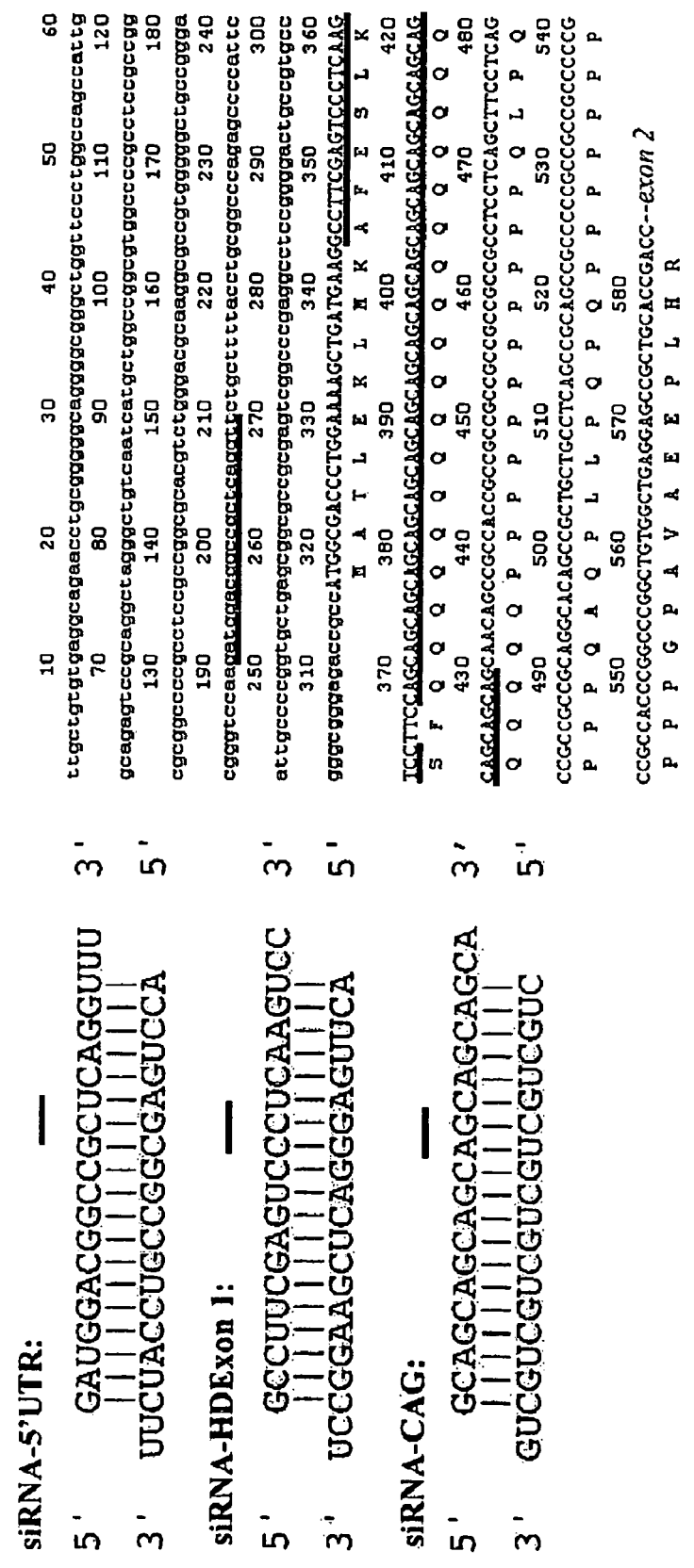

Three types of RNAs were designed based on the exon 1 region of a huntingtin gene (NCBI accession NO: L12392 and the $1^{st}$ to $584^{th}$ of NM_002111; SEQ ID NO: 1) (FIG. 1). Three types of RNAs composed of 21 nucleotides, that is, (1) siRNA-HDexon 1, sense-strand: the $343^{rd}$ to $363^{rd}$ of SEQ ID NO: 1; GCCUUCGAGUCCCUCAAGUCC (SEQ ID NO: 3), antisense-strand: complementary to the $341^{st}$ to $361^{st}$ of SEQ ID NO: 1; UCCGGAAGCUCAGGGAGUUCA (SEQ ID NO: 4), (2) siRNA-5'UTR, sense-strand: the $190^{th}$ to $210^{th}$ of SEQ ID NO: 1; GAUGGACGGCCGCUCAGGUUU (SEQ ID NO: 5), antisense-strand: complementary to the $188^{th}$ to $208^{th}$ of SEQ ID NO: 1; UUCUACCUGCCGGC-GAGUCCA (SEQ ID NO: 6), (3) siRNA-CAG, sense-strand: the $367^{th}$ to $387^{th}$ of SEQ ID NO: 1; GCAGCAGCAGCAG-CAGCAGCA (SEQ ID NO: 7), antisense-strand: complementary to the $409^{th}$ to $429^{th}$ of SEQ ID NO: 1; GUCGUCGUCGUCGUCGUC (SEQ ID NO: 8) (See FIG. 1 for all the three types), were chemically synthesized and subjected to HPLC purification (Xeragon, USA). For double-stranded siRNAs, 20 mM of sense- and antisense-strand RNAs were annealed in annealing buffer (100 mM potassium acetate, 2 mM magnesium acetate, 30 mM HEPES, adjusted to pH 7.4 with 0.1 N potassium hydroxide, stored at 4° C.). The reaction mixture was heated at 95° C. for 5 minutes, then gradually cooled down to 37° C. for 1.5 hours, then left for 6 to 20 hours at room temperature. Annealed siRNAs were stored at −20° C. or −80° C. until use.

(Plasmid Construction)

Two types of expression vectors, 5'UTR exon 1 and HDexon 1 were constructed. Both types of the constructs, one with 5'UTR and the other without 5'UTR, were made by using the normal (containing 34 CAG repeats) or mutant (containing 35 or more CAG repeats) HD genes. The constructs were fused in-frame with human HD partial 5'UTR and full length of exon 1 pd1EGFP-N1 (de-stabled EGFP, Clontech) EGFP (see FIG. 2).

(Cell Lines and Medium)

Three types of cell lines which are established from different kinds of genesis; COS-7 cells (African green monkey fibroblasts), SH-sy5y cells (human neuroblastoma), and Neuro-2A cells (mouse neuroblastoma); were used. COS-7 cells, and SH-sy5y and Neuro-2A cells were respectively cultured in Minimum Essential Medium-Alpha Medium (Gibco BRL) and in Dulbecco's Modified Eagle's Medium (Gibco BRL). Besides, in each medium, 10% heat inactivated fetal bovine serum, 10 units/ml of penicillin (Meiji), and 50 μg/ml of streptomycin (Meiji) were respectively supplemented.

(Transfection)

Cultured cells disseminated 24 hours before transfection were proliferated in medium with 10% of FBS but without antibiotics. Construct plasmid and siRNAs were introduced into the cells by using 2 types of transfection reagents.

a. Effectene (Qiagen, Germany): 96-well plate was used for culturing cells and transfection experiments. Around 40 to 60% of confluent cells were precultured for 24 hours before transfection following manufacturer's instructions. Each well was added with 0.5 μL of Effectene reagent and the results were analyzed 24 hours later.

b. Lipofectamine 2000 (Invitrogen, USA): Around 80% of confluent cells were precultured for 24 hours before transfection following manufacturer's instructions. Each well was added with 0.3 μL of Lipofectamine 2000 reagent. In addition, the expression levels in the experiments with either a or b reagents, were analyzed 24 to 48 hours later.

c. siRNAs were introduced into SH-sy5y cells in order to examine the effects of siRNA on the suppression of human endogenous HD gene expression, by using Lipofectamine 2000 reagent. The cells were collected 48 hours after the transfection and total RNAs were extracted by using Trizol (Invitrogen, USA).

(Quantitation Assessment of siRNA Effect)

Cultured plates were observed under fluorescence microscopy 24 and 48 hours after transfection. In order to perform a quantitation evaluation of the effect of siRNAs, the GFP fluorescence was measured (excitation at 485 nm, emission at 538 nm) by using Wallac 1420 ARVO sx (ParkinElmer, USA) or FluoreScan II.

(Quantitation Estimation of mRNA Levels)

Quantitation estimation of transgenic HD exon 1-EGFP mRNA was performed by real time RT-PCR using LightCycler (Roche, USA). The effects of siRNA-HDexon 1 against endogenous HD expression in SH-sy5y cells were measured by quantitation RT-PCR using LightCycler (Roche, USA). As a control, the expression levels of GAPDH and β-actin were measured for each sample.

(Mammal Animal Models)

Mouse model for Huntington's disease (systematic name: B6CBA-Tg(HDexon1)62oGpb/J, generic name: R6/2, purchased from: The Jackson Laboratory, USA) is used. These mice are hemizygotes implanted with ovaries of transgenic female mice F1 that were introduced with partial huntingtin genes (exon 1, containing huntingtin promoters and a region of 114 CAG repeats), around 1 kb of human genes. Symptoms were developed in the mice from around 9 to 11 weeks old, showing clinical symptoms such as weight loss, tremor, unsteady gait, and convulsive seizure, all of the mice die by the age of 15 weeks. As the neuropathological findings, nuclear inclusions stained with anti-huntingtin antibodies and anti-ubiquitin antibodies are detected in almost all the nuclei of neuronal cells.

(Administration Method into Living Body)

A 5 μl amount of the complexes (containing around 200 ng of siRNA-HD exon) of siRNA-HD exon and Lipofectamine 2000 (Invitrogene, USA) was infused into the brains of 2-day-old mice, using 50 μl Hamilton syringe. The needle was inserted at 1 mm posterior to and 1 mm right to bregma into the depth of 2 mm.

(Quantitation Assessment of siRNA Effect in Living Body)

Quantitation assessment of mRNA levels: after intracranial adminnistration, quantitation analysis of the mRNAs of mutant huntingtin were performed by real time PT-PCR using ABI 7700 sequence detector system (ABI, USA). Primer sequences: 5'-CGCCGCCTCCTCAGCTTCCT-3' (forward; SEQ ID NO: 9), 5'-GCGGTGGTGGCGGCGGCGGCT-3' (reverse; SEQ ID NO: 10). As internal controls, GAPDH and β-actin were used.

Histopathologic quantitation analysis: after preperfusion with PBS for 5 minutes at room temperature, purfusion fixation was performed with 4% paraformaldehyde (PFA), and brain extract was immediately prepared, then quickly postfixation was performed in the same fixative overnight at 4° C. After that, the brain tissue was embedded with paraffin, the sections of 4 mm thickness were made. Immunostaining was performed using ABC method (Vectorstain Elite ABC kit, Vector Labs, Burlinggame, USA). Rabbit anti-ubiquitin polyclonal antibody (1:100; Dako, CA, USA) and mouse anti-huntingtin monoclonal antibody (mEM48, 1:500; Chemicon, Temecula, USA) were used. After DAB staining, poststaining was performed with hematoxylin, and dehydration, transparence, inclusion, and then examined by light microscopy and pictures were taken.

Quantitation analysis at individual levels:

Weight change: The body weights were measured every week from 4 weeks of age.

Tail suspension test: mice were hung by their tails and the time taken for the mice to take a posture that their hind legs curl up ventrally was measured every week, from 4 to 14 weeks of age, until the mice were determined to have "an onset" (of the disease). As the judgment standard, it was determined as "onset" when the time was 15 seconds or less.

Survival time: The life spans (days) of the mice kept individually and died by disease were recorded.

[Results]

(In Vitro Data)

Figure 3:
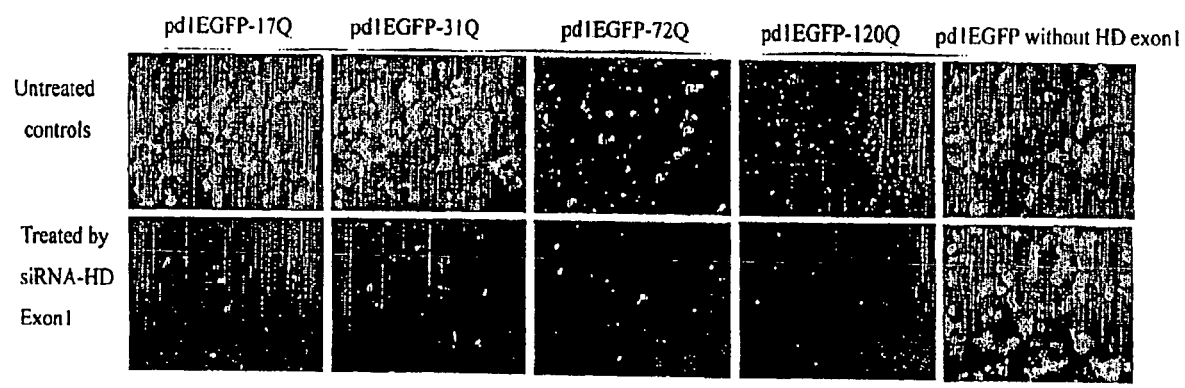
FIG. 3 shows the pictures of COS-7 cells co-transfected with siRNA-HDexon 1 in the Example of the present invention, which were observed under fluorescence microscope.
Figure 4:
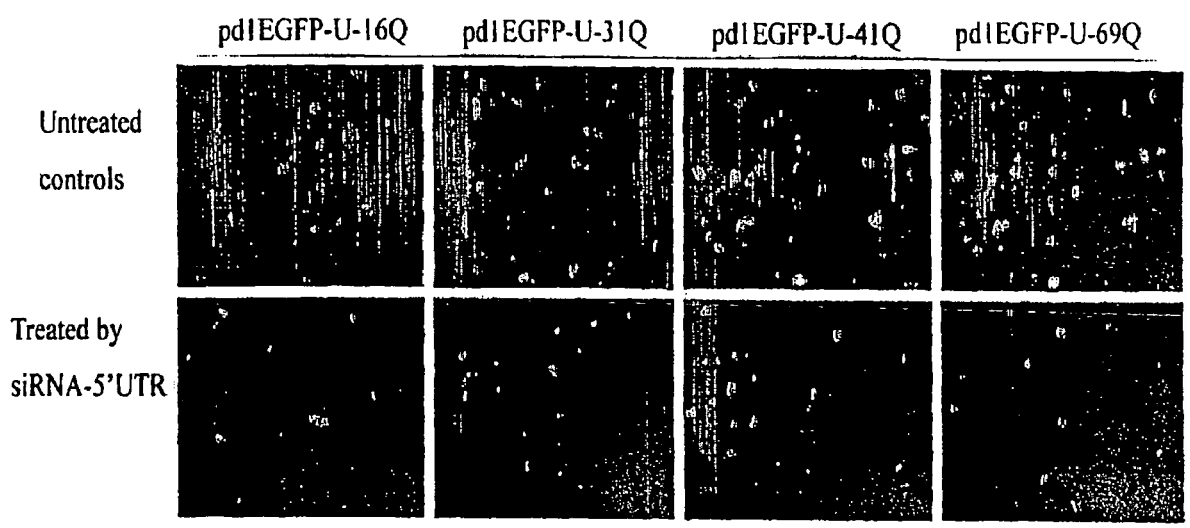
FIG. 4 shows the pictures of COS-7 cells co-transfected with siRNA-5'UTR in the Example of the present invention, which were observed under fluorescence microscope.
Figure 5:
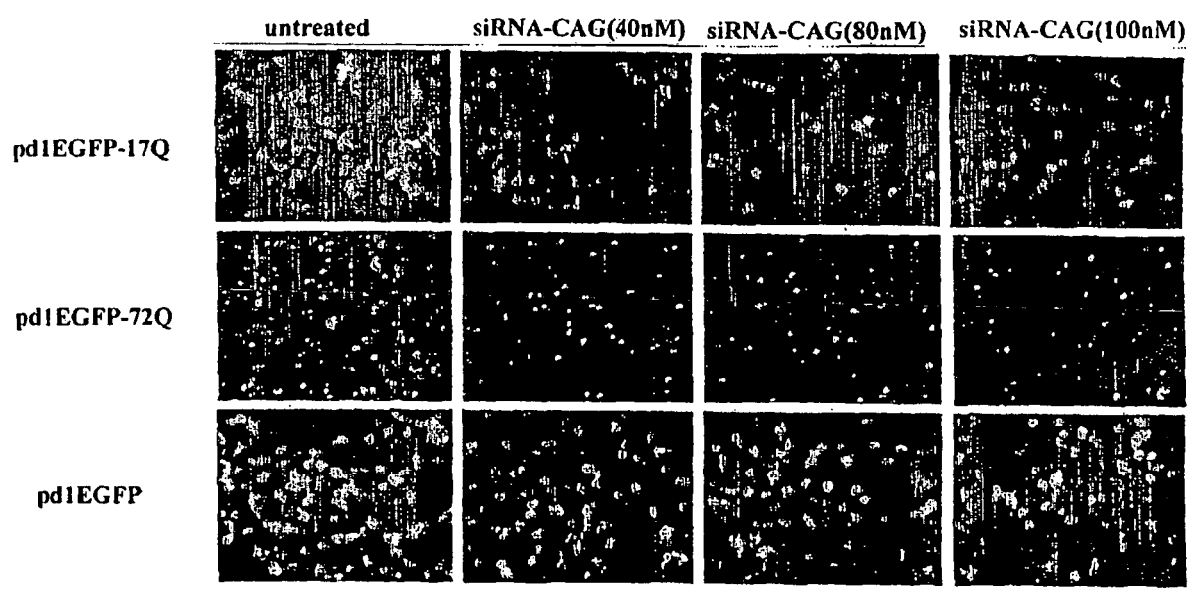
FIG. 5 shows the pictures of COS-7 cells co-transfected with siRNA-CAG in the Example of the present invention, which were observed under fluorescence microscope.
Figure 6:
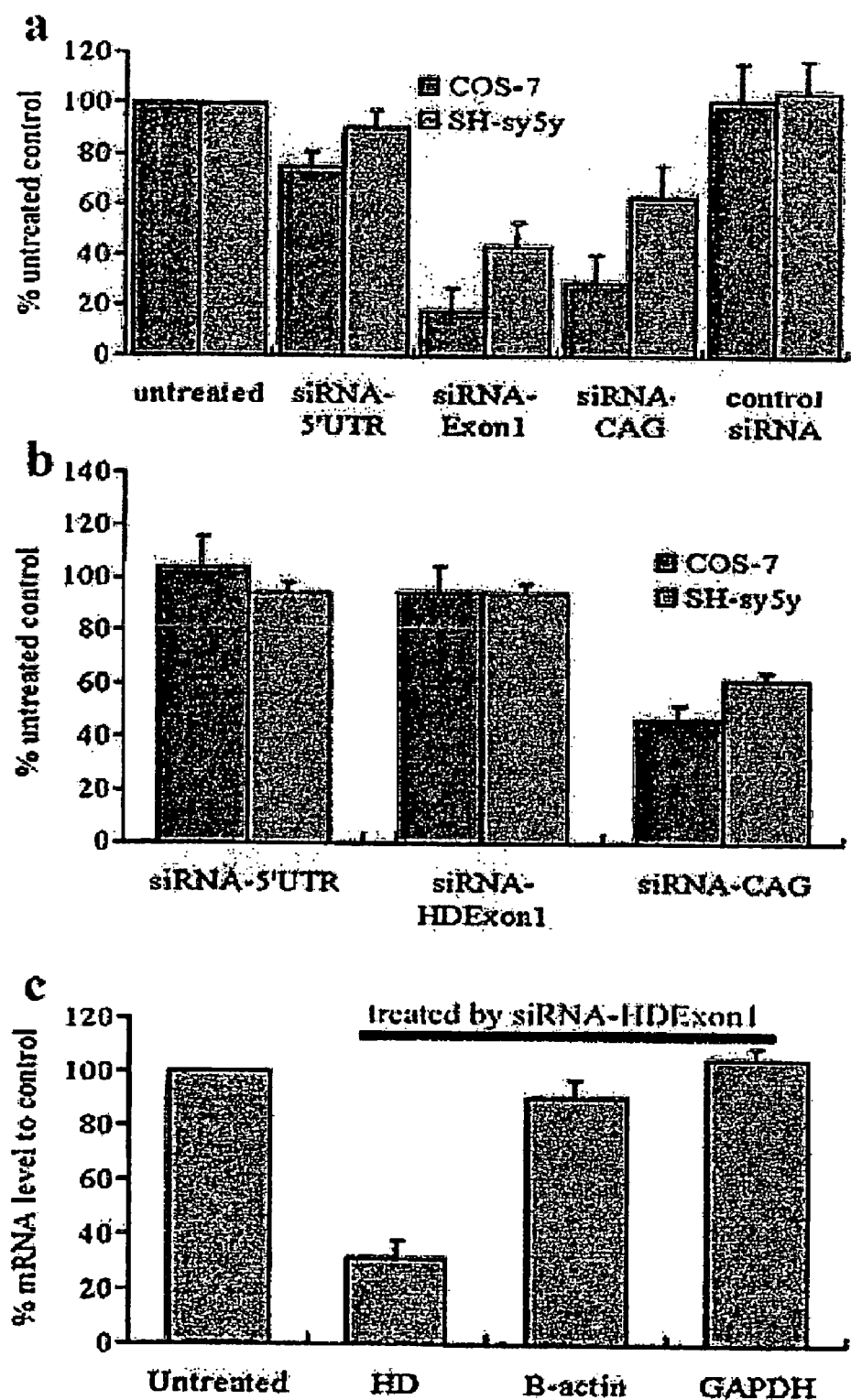
FIG. 6 ; a. shows the effects of siRNAs, and that the effect of siRNAs differs depending on target positions and cell types, by calibrating untreated controls (4 independent experiments) at the average of EGFP fluorescence; b. shows the results that the parent vectors (without HDexon 1) were co-transfected with three types of siRNAs respectively; c. shows the average relative mRNA amounts of HD, β-actin, and GAPDH against the untreated controls.

The suppression effect of synthesized siRNAs was analyzed by cotransfecting with expression constructs, using COS-7 cultured cells. As a result, although the effect differed from one siRNA to another, the siRNAs of the present invention demonstrated that the expression of exon 1 of the exogenous HD gene was suppressed (see reference pictures 1-3 and FIG. 3-5). The siRNA-HDexon 1 among the tested tree types of siRNAs showed extremely high effect and suppression of the 80% or more of the targeted transgene expression when the final concentration of the siRNAs in medium was 40 nM. In contrast, the other 2 types of siRNAs (siRNA-5'UTR, siRNA-CAG) only showed moderate to minor effect (FIG. 6a, estimated from measurement by GFP fluorescence). Furthermore, it was observed by the present invention that the suppression effect of the 2 types of siRNAs was gene-specific, but that the suppression effect of siRNA-CAG was non-specific and suppressed the expression of the vectors without HD gene exon 1 (FIG. 6b). As expected, siRNA induced the mRNA degradation of the targeted transfected gene predicted by quantitation RT-PCR.

Huntington's disease (HD) is caused by selective neuronal cell death and the suppression of the HD expression in neuronal cells is the most important. Neuronal cells were considered to be most-resistant to RNAi (Gene 263, 103-112, 2001), however, it was demonstrated that RNAi functions properly in neuronal cells (PNAS 99, 18, 11926-11929, 2002). Experiments wherein siRNAs and expression constructs were transfected into SH-sy5y (human neuroblastoma) cultured cells by the present invention showed that the siRNA-HDexon 1 was less effective compared with the COS-7 cultured cells, however, the other 2 types of the siRNAs had only low effect or no effect (FIG. 6a).

The above-mentioned result demonstrated that siRNA-HDexon 1 had the most suppressive effect on the expression of Huntington's disease (HD); therefore, the effect of siRNA-HDexon 1 on endogenous HD gene expression in SH-sy5y cells was tested. The quantitation measurement of HD mRNA showed that 60% or more of the endogenous HD gene expression was inhibited 48 hours after using siRNA-HDexon 1. In the meantime, mRNA levels of both GAPDH and β-actin did not change significantly; therefore it was proved that the suppression of HD gene by siRNA-HDexon 1 was HD gene-specific (FIG. 6c).

(In Vivo Data)

Figure 7:
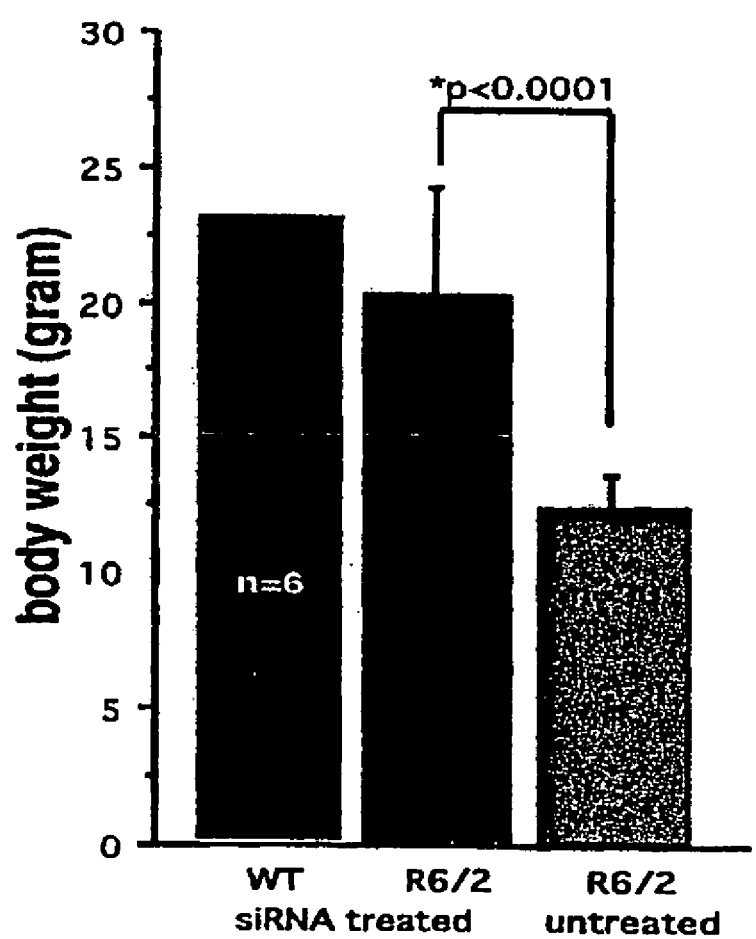
FIG. 7 shows that the weight loss of the siRNA-HDexon treated R6/2 mice in the Example of the present invention was significantly suppressed at 14 weeks of age. The comparison between siRNA-HDexon treated group and siRNA-HDexon untreated group shows a significant drop in weight of the untreated group (gray bar) and meanwhile only a little drop in weight of the treated group (red bar), compared with the wild type (WT; black bar).
Figure 8:
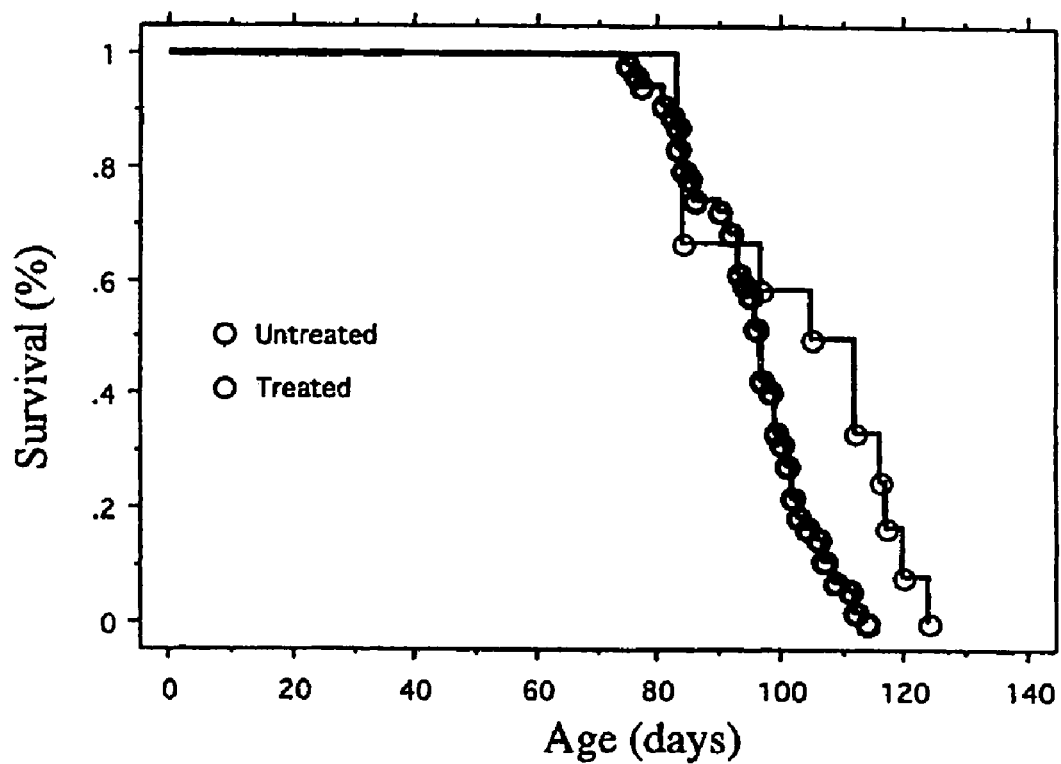
FIG. 8 shows that the survival time of the siRNA-HDexon treated R6/2 mice in the Example of the present invention was significantly prolonged.

It was found that the effect at individual levels in siRNA-HDexon treated group significantly delayed in tail suspension test, which was used to identify the onset. On the other hand, after the mice reached 5 weeks of age, the weight loss of the siRNA-HDexon treated R6/2 mice significantly improved compared with continuous weight loss of the untreated R6/2 mice (FIG. 7). The comparison between the cumulative probabilities of survival curves of siRNA-HDexon treated and untreated (Kaplan-Meter method) showed that the survival time of the treated group (red line) was also significantly improved compared with that of the untreated group (black line) (FIG. 8).

Figure 9:
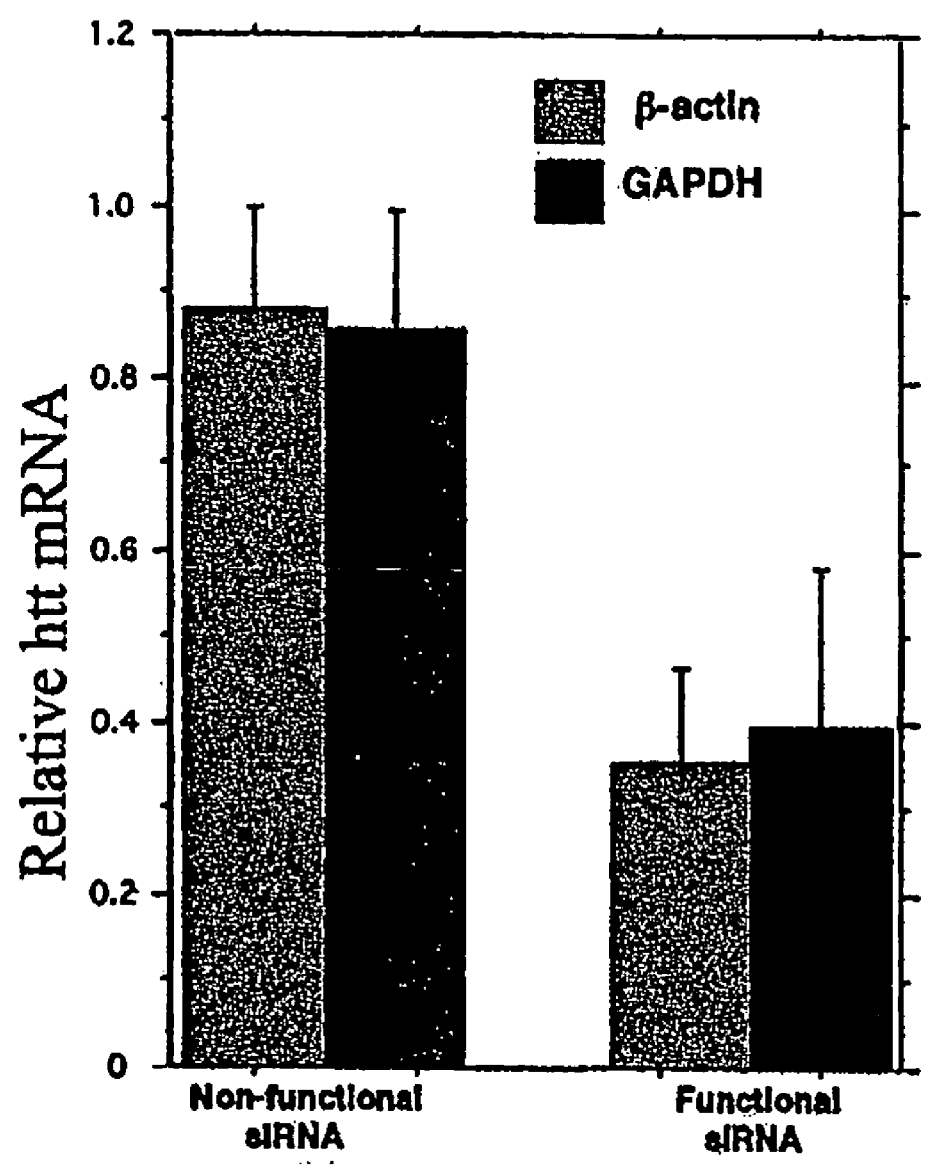
FIG. 9 shows the results of quantitation RT-PCR, which demonstrate the suppression of the expression level of mutant huntingtin mRNA in striatum 48 hours after intracerebral injection to the siRNA-HDexon treated R6/2 mice in the Example of the present invention. Vertical axis indicates the relative value of mutant huntingtin mRNA levels, gray bars show the levels when β-actin was used as the internal standard, and red bars show the levels when GAPDH was used as the internal standard.
Figure 10:
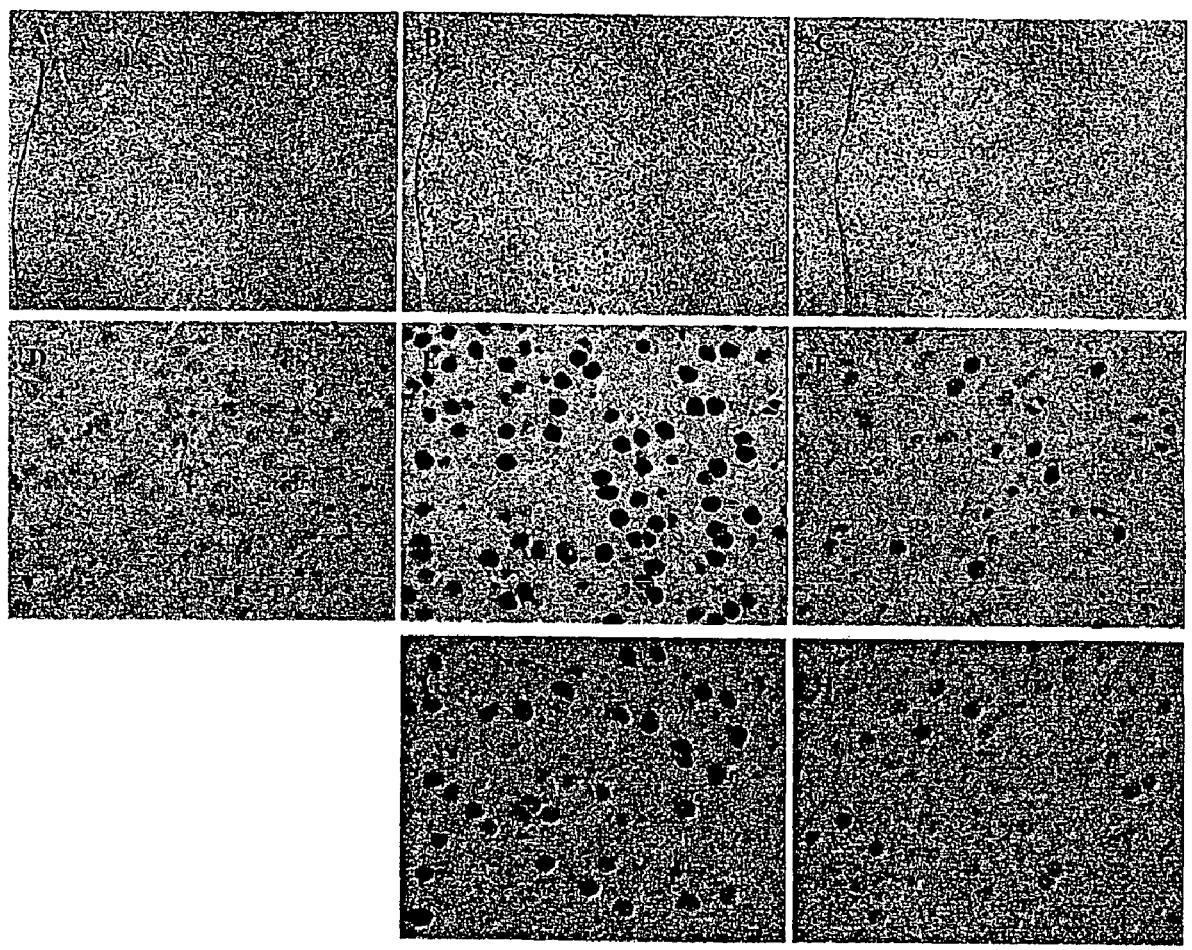
FIG. 10 shows the pictures that the occurrence rate of the neuronal nuclear inclusion bodies in the striatum significantly decreased in the siRNA-HDexon treated R6/2 mice in the Example of the present invention. A-F and G-H show the staining with anti-huntingtin antibodies and anti-ubiquitin antibodies, respectively.

In addition to this clinical effect, the level of the mRNA expression of mutant huntingtin in striatum was reduced by 60% in the brain 48 hours after the injection (FIG. 9). As the result of immunostaining using anti-ubiquitin and anti-huntingtin antibodies pathologically, in siRNA-HDexon treated group, the occurrence rates of both ubiquitin- and huntingtin-positive nuclear aggregates in striatum were significantly decreased (FIG. 10). FIG. 10 shows the immunostaining image of huntingtin- and ubiquitin-positive nuclear inclusion bodies in the striatum of 10-week-old R6/2 transgenic mice. A-F and G-H show the dye-affinities for huntingtin and ubiquitin respectively. In case of huntingtin, the distinct strong positive findings of nuclear staining were seen in R6/2 mice (B, E, C, and F); in contrast, no finding was seen at all in wild type mice (A and D). On the contrary, in siRNA-HDexon treated mice (C and F), the number of the nuclear inclusion bodies was significantly decreased compared to the untreated controls (B and E). Similarly, the number of the ubiquitinated nuclear inclusion bodies in siRNA-HDexon treated mice was also decreased (G was untreated; H was siRNA-HDexon treated).

As described above, the transcriptional levels of huntingtin genes were suppressed in living bodies and the new formation of nuclear aggregates was decreased in R6/2 mice with only one-time injection, as a result, the longevity of the mice was extended.

[Discussion]

It is an ideal approach to suppress the expression of mutant alleles (carrying 35 or more CAG repeats) before the occurrence of toxicity. On the other hand, the combinations of siRNA and construct each contained deferent length of CAG repeats (14-149) showed that the suppression effect was irrelevant to the length of CAG repeats.

The present study demonstrated that one of the siRNAs efficiently mediated the specific suppression of the expression of Huntington's disease (HD). Since RNAi was demonstrated to be also functional in adult mice (Nature 418, 38-39, 2002), the efficient suppression of HD expression is useful to study the not-yet-understood huntingtin functions after suppressing the endogenous huntingtin in various types of cells and living bodies of animal models. Usage of siRNA technology as a treatment method can be a strategy of the treatment for HD patients (Mol. Med. Today 3, 175-183, 1997). The progression of the disease can be arrested by the suppression of HD expression within the specific region. Because it dose not seem that huntingtin functions are observed sensitively (or below detection limit) to the quantity of the gene products expressed in HD patients (Cell 101, 57-66, 2000).

INDUSTRIAL APPLICABILITY

In the present invention, double-stranded RNAs (dsRNAs) were successfully produced to suppress a huntingtin gene expression specifically and efficiently. The dsRNAs of the present invention were made by determination of dsRNA sequence resulting from searching the scarcity of sequence in genome and reviewing the predictive second structure of huntingtin gene product. The dsRNAs of the present invention suppress the gene expression by RNA interference, but the effect is specific and efficient, and suppresses the huntingtin gene expression specifically and efficiently. Particularly, the short double-stranded RNAs (siRNAs) constructed in the present invention, produce significant suppression efficiency and are greatly expected as a drug for the realization of genetic therapy of Huntington's disease.

Since Huntington's disease is progressive and inheritable disease for which useful therapy has not established, it is expected to become a useful method when the expression of the mutant gene that is cause of the disease is specifically and efficiently suppressed. The application of RNAi (RNA interference) by the double-stranded RNAs (dsRNAs) of the present invention, is a promising tool to achieve a goal of the above-mentioned idea, and therefore the present invention contributes significantly to development of the treatment method for Huntington's disease.

Moreover, dentato- rubral-pallidoluysian atrophy, spinocerebellar ataxia, Kennedy-Alter-Sung disease, Machado-Joseph disease and the like are triplet repeat diseases having the common pathogenetic mechanism with Huntington's disease. Thus the establishment of the treatment method for Huntington's disease by the present invention can expand the capability of overcoming these diseases having certain characteristics in common.

The invention claimed is:

1. A double-stranded RNA which is composed of sense- and antisense-strand RNAs, fully homologous to the sequence composed of base sequences shown in SEQ. ID NOs: 3 and 4 in the sequence listing, wherein the double-stranded RNA can inhibit huntington gene expression.

2. The double-stranded RNA according to claim 1 prepared from synthesized sense- and antisense-strand RNAs.

3. The double-stranded RNA according to claim 1, which is prepared from sense- and antisense-strand RNAs generated by using gene recombination.

4. The double-stranded RNA according to claim 3, wherein the sense- and antisense-strand RNAs generated by using gene recombination are prepared by obtaining RNAs which are generated by introducing a expression vector incorporated DNA capable of transcribing respectively the RNAs, into a host cell.

5. A huntington gene expression inhibitor composed of the double-stranded RNA according to any one of claims 1, and 2 to 4.

6. A huntington gene expression inhibitor composed of a fusion product, wherein the double-stranded RNA according to any one of claims 1, and 2 to 4 is added to a TAT sequence, a protein transduction domain derived from HIV-1.

7. A huntington gene expression inhibitor composed of a complex formed from the double-stranded RNA according to any one of claims 1, and 2 to 4 and a positively-charged ribosome/lipid.

8. A huntington gene expression inhibitor composed of an expression vector incorporating a DNA capable of transcribing the double-stranded RNA according to claim 1.

9. A remedy of Huntington's disease containing the huntington gene expression inhibitor according to claim 5 as an effective ingredient.

10. The remedy of Huntington's disease according to claim 9 further containing a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,589,189 B2 | Page 1 of 1 |
| APPLICATION NO. | : 10/556711 | |
| DATED | : September 15, 2009 | |
| INVENTOR(S) | : Ichiro et al. | |

It is certified that error appears in the above-identified patent and that said Letters Patent is hereby corrected as shown below:

Title page,
Item (57) ABSTRACT,
Lines 1, 3, 4, 7 and 14, "huntington" should read --huntingtin--.

Column 15, claim 1 and claim 5,
Lines 30 and 42, "huntington" should read --huntingtin--.

Column 16, claim 6 and claim 7,
Lines 25, 29, and 33, "huntington" should read --huntingtin--.

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO.          : 7,589,189 B2
APPLICATION NO.     : 10/556711
DATED               : September 15, 2009
INVENTOR(S)         : Kanazawa et al.

Page 1 of 1

It is certified that error appears in the above-identified patent and that said Letters Patent is hereby corrected as shown below:

On the Title page,

Item (12),

Line 2, "Ichiro et al." should read --Kanazawa et al.--.

Item (75) Inventors:,

Line 1, "Kanazawa Ichiro" should read --Ichiro Kanazawa--.

Signed and Sealed this
Fifteenth Day of March, 2011

David J. Kappos
*Director of the United States Patent and Trademark Office*

SEQUENCE LISTING

```
<160> NUMBER OF SEQ ID NOS: 10

<210> SEQ ID NO 1
<211> LENGTH: 584
<212> TYPE: DNA
<213> ORGANISM: Homo sapiens

<400> SEQUENCE: 1
ttgctgtgtg aggcagaacc tgcgggggca ggggcgggct ggttccctgg ccagccattg      60
gcagagtccg caggctaggg ctgtcaatca tgctggccgg cgtggcccct cctccgccgg     120
cgcggccccg cctccgccgg cgcacgtctg ggacgcaagg cgccgtgggg gctgccggga     180
cgggtccaag atggacggcc gctcaggttc tgcttttacc tgcggcccag agccccattc     240
attgccccgg tgctgagcgg cgccgcgagt cggcccgagg cctccgggga ctgccgtgcc     300
gggcgggaga ccgccatggc gaccctggaa aagctgatga aggccttcga gtccctcaag     360
tccttccagc agcagcagca gcagcagcag cagcagcagc agcagcagca gcagcagcag     420
cagcagcagc aacagccgcc accgccgccg ccgccgccgc cgcctcctca gcttcctcag     480
ccgccgccgc aggcacagcc gctgctgcct cagccgcagc cgccccgcc gccgccccg      540 ccgccacccg gcccggctgt ggctgaggag ccgctgcacc gacc                       584

<210> SEQ ID NO 2
<211> LENGTH: 89
<212> TYPE: PRT
<213> ORGANISM: Homo sapiens

<400> SEQUENCE: 2

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln
            20                  25                  30

Gln Gln Gln Gln Gln Gln Gln Gln Pro Pro Pro Pro Pro Pro Pro
        35                  40                  45

Pro Pro Pro Gln Leu Pro Gln Pro Pro Pro Gln Ala Gln Pro Leu Leu
```

```
                50                    55                    60
Pro Gln Pro Gln Pro Pro Pro Pro Pro Pro Pro Pro Pro Gly Pro
65                  70                    75                    80

Ala Val Ala Glu Glu Pro Leu His Arg
                85

<210> SEQ ID NO 3
<211> LENGTH: 21
<212> TYPE: RNA
<213> ORGANISM: Artificial
<220> FEATURE:
<223> OTHER INFORMATION: siRNA-HD Exon1 sense RNA

<400> SEQUENCE: 3
gccuucgagu cccucaaguc c                                              21

<210> SEQ ID NO 4
<211> LENGTH: 21
<212> TYPE: RNA
<213> ORGANISM: Artificial
<220> FEATURE:
<223> OTHER INFORMATION: siRNA-HD Exon1 antisense RNA

<400> SEQUENCE: 4
uccggaagcu cagggaguuc a                                              21

<210> SEQ ID NO 5
<211> LENGTH: 21
<212> TYPE: RNA
<213> ORGANISM: Artificial
<220> FEATURE:
<223> OTHER INFORMATION: siRNA-5' UTR sense RNA

<400> SEQUENCE: 5
gauggacggc cgcucagguu u                                              21

<210> SEQ ID NO 6
<211> LENGTH: 21
<212> TYPE: RNA
<213> ORGANISM: Artificial
<220> FEATURE:
<223> OTHER INFORMATION: siRNA-5' UTR antisense RNA

<400> SEQUENCE: 6
uucuaccugc cggcgagucc a                                              21

<210> SEQ ID NO 7
<211> LENGTH: 21
<212> TYPE: RNA
<213> ORGANISM: Artificial
<220> FEATURE:
<223> OTHER INFORMATION: siRNA-CAG sense RNA

<400> SEQUENCE: 7
gcagcagcag cagcagcagc a                                              21

<210> SEQ ID NO 8
<211> LENGTH: 21
<212> TYPE: RNA
<213> ORGANISM: Artificial
<220> FEATURE:
<223> OTHER INFORMATION: siRNA-CAG antisense RNA

<400> SEQUENCE: 8
gucgucgucg ucgucgucgu c                                              21
```

-continued

```
<210> SEQ ID NO 9
<211> LENGTH: 20
<212> TYPE: DNA
<213> ORGANISM: Artificial
<220> FEATURE:
<223> OTHER INFORMATION: forward primer

<400> SEQUENCE: 9
cgccgcctcc tcagcttcct                                                      20

<210> SEQ ID NO 10
<211> LENGTH: 21
<212> TYPE: DNA
<213> ORGANISM: Artificial
<220> FEATURE:
<223> OTHER INFORMATION: reverse primer

<400> SEQUENCE: 10
gcggtggtgg cggcggcggc t                                                    21
```